US012599302B2

(12) United States Patent
Ashok et al.

(10) Patent No.: US 12,599,302 B2
(45) Date of Patent: Apr. 14, 2026

(54) VOLUMETRIC OCT IMAGE DATA PROCESSING

(71) Applicant: OPTOS PLC, Dunfermline (GB)

(72) Inventors: Praveen Ashok, Dunfermline (GB);
Alan Anderson, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 1041 days.

(21) Appl. No.: 17/492,583

(22) Filed: Oct. 2, 2021

(65) Prior Publication Data

US 2022/0142471 A1      May 12, 2022

(30) Foreign Application Priority Data

Nov. 12, 2020    (EP) ..................................... 20207153

(51) Int. Cl.
A61B 3/10          (2006.01)
G16H 30/40      (2018.01)

(52) U.S. Cl.
CPC ............. A61B 3/102 (2013.01); G16H 30/40 (2018.01)

(58) Field of Classification Search
CPC ..... A61B 3/102; A61B 3/0025; A61B 3/1015; A61B 3/113; A61B 3/117; A61B 3/1173; A61B 3/12; A61B 3/1225; G16H 30/40; G06T 2207/10101; G06T 2207/30041; G06T 2207/10072; G06T 2207/20;
(Continued)

(56) References Cited

U.S. PATENT DOCUMENTS

| | | | |
|---|---|---|---|
| 7,997,729 B2 | 8/2011 | McLean et al. | |
| 9,044,164 B2 | 6/2015 | Hacker et al. | |
| 2009/0147801 A1 | 6/2009 | Terashima | |

(Continued)

FOREIGN PATENT DOCUMENTS

| | | |
|---|---|---|
| JP | 2009-141692 A | 6/2009 |
| WO | 2013/059303 A1 | 4/2013 |

(Continued)

OTHER PUBLICATIONS

European Search Report issued on Apr. 30, 2021, in European patent application No. 20 20 7153 (7 sheets).
(Continued)

*Primary Examiner* — Travis S Fissel
(74) *Attorney, Agent, or Firm* — Faegre Drinker Biddle & Reath LLP

(57)                    ABSTRACT
A method of processing C-scan data, which comprises a sequence of B-scans of an imaging target acquired by an OCT imaging system, to generate correction data for compensating for axial displacements between B-scans in the sequence caused by a relative motion of the OCT imaging system and the imaging target that varies a distance therebetween during acquisition of the B-scans, the correction data being generated by determining, for each pair of adjacent B-scans of a plurality of pairs of adjacent B-scans in the sequence, a respective indicator of an axial shift between respective representations of a common ocular feature in the adjacent B-scans; and determining, from a variation of the determined indicators with locations of the corresponding pairs of adjacent B-scans in the sequence, a first frequency component of the variation which is indicative of the relative motion during acquisition of the B-scans.

24 Claims, 9 Drawing Sheets

(58) Field of Classification Search
CPC ......... G06T 2207/20012; G06T 7/0012; G06T
7/33; G06T 7/0014; G06T 7/0002; G06T
7/0016
USPC ........................................................ 351/206
See application file for complete search history.

(56) References Cited

U.S. PATENT DOCUMENTS

| | | |
|---|---|---|
| 2014/0029826 A1 | 1/2014 | Pintal |
| 2014/0236002 A1* | 8/2014 | Wang .................... A61B 3/102 600/427 |
| 2022/0039648 A1* | 2/2022 | Draelos ................... A61B 3/13 |

FOREIGN PATENT DOCUMENTS

| | | |
|---|---|---|
| WO | 2015/120055 A1 | 8/2015 |
| WO | 2020/160097 A1 | 8/2020 |
| WO | 2021019025 A1 | 2/2021 |

OTHER PUBLICATIONS

Notice of Reasons for Rejection issued in Japanese Patent Application No. 2021-179160 dated Oct. 11, 2022 (2 sheets); English translation attached (2 sheets).

* cited by examiner

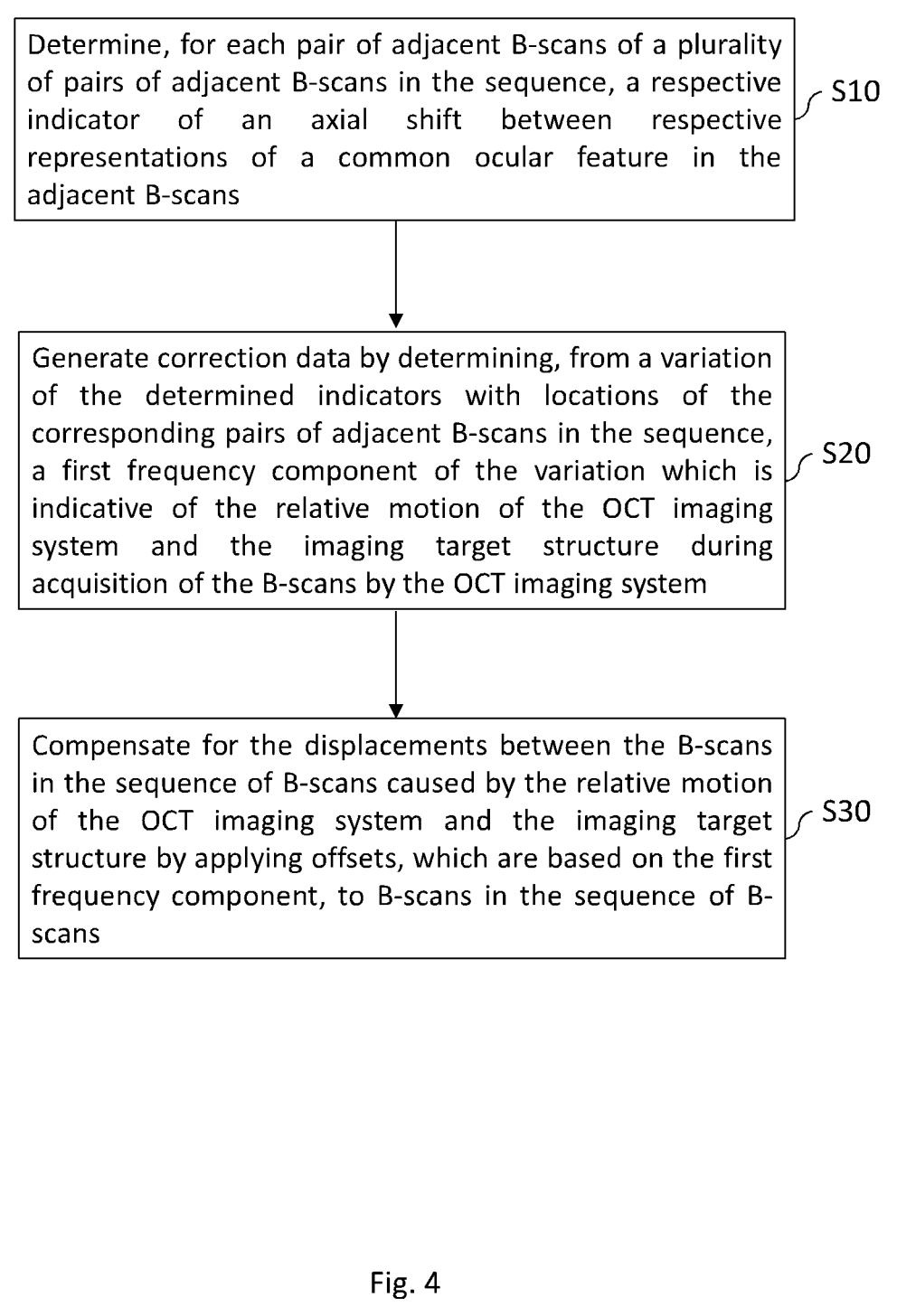

Determine, for each pair of adjacent B-scans of a plurality of pairs of adjacent B-scans in the sequence, a respective indicator of an axial shift between respective representations of a common ocular feature in the adjacent B-scans    ⌐ S10

Generate correction data by determining, from a variation of the determined indicators with locations of the corresponding pairs of adjacent B-scans in the sequence, a first frequency component of the variation which is indicative of the relative motion of the OCT imaging system and the imaging target structure during acquisition of the B-scans by the OCT imaging system    ⌐ S20

Compensate for the displacements between the B-scans in the sequence of B-scans caused by the relative motion of the OCT imaging system and the imaging target structure by applying offsets, which are based on the first frequency component, to B-scans in the sequence of B-scans    ⌐ S30

Fig. 4

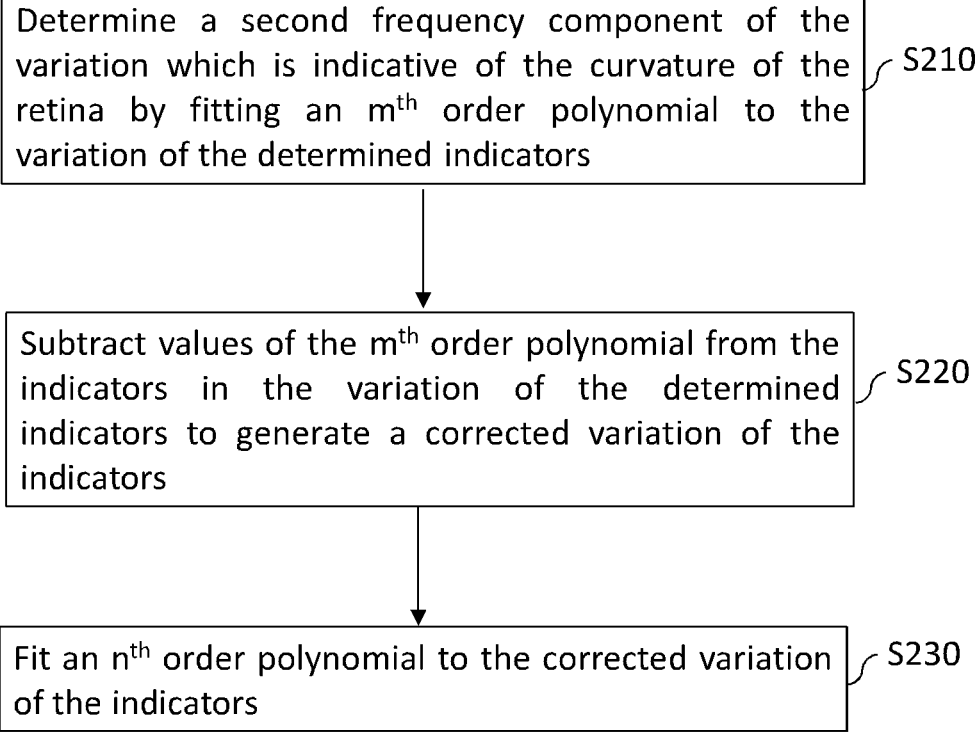

Determine a second frequency component of the variation which is indicative of the curvature of the retina by fitting an $m^{th}$ order polynomial to the variation of the determined indicators — S210

Subtract values of the $m^{th}$ order polynomial from the indicators in the variation of the determined indicators to generate a corrected variation of the indicators — S220

Fit an $n^{th}$ order polynomial to the corrected variation of the indicators — S230

Fig. 6

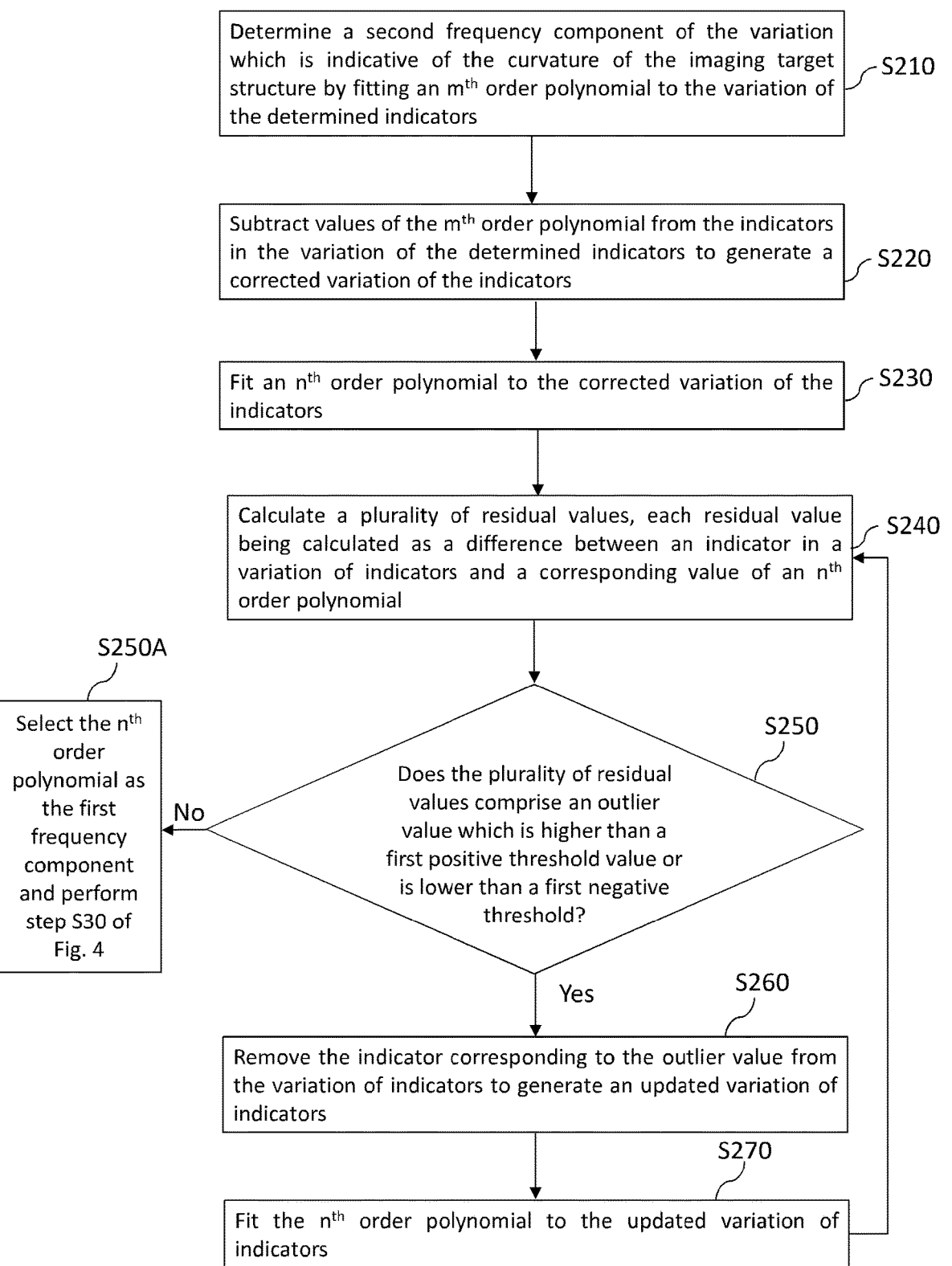

Determine a second frequency component of the variation which is indicative of the curvature of the imaging target structure by fitting an $m^{th}$ order polynomial to the variation of the determined indicators ⌐S210

Subtract values of the $m^{th}$ order polynomial from the indicators in the variation of the determined indicators to generate a corrected variation of the indicators ⌐S220

Fit an $n^{th}$ order polynomial to the corrected variation of the indicators ⌐S230

Calculate a plurality of residual values, each residual value being calculated as a difference between an indicator in a variation of indicators and a corresponding value of an $n^{th}$ order polynomial ⌐S240

S250A

Select the $n^{th}$ order polynomial as the first frequency component and perform step S30 of Fig. 4

No

Does the plurality of residual values comprise an outlier value which is higher than a first positive threshold value or is lower than a first negative threshold? S250

Yes S260

Remove the indicator corresponding to the outlier value from the variation of indicators to generate an updated variation of indicators

S270

Fit the $n^{th}$ order polynomial to the updated variation of indicators

Fig. 7

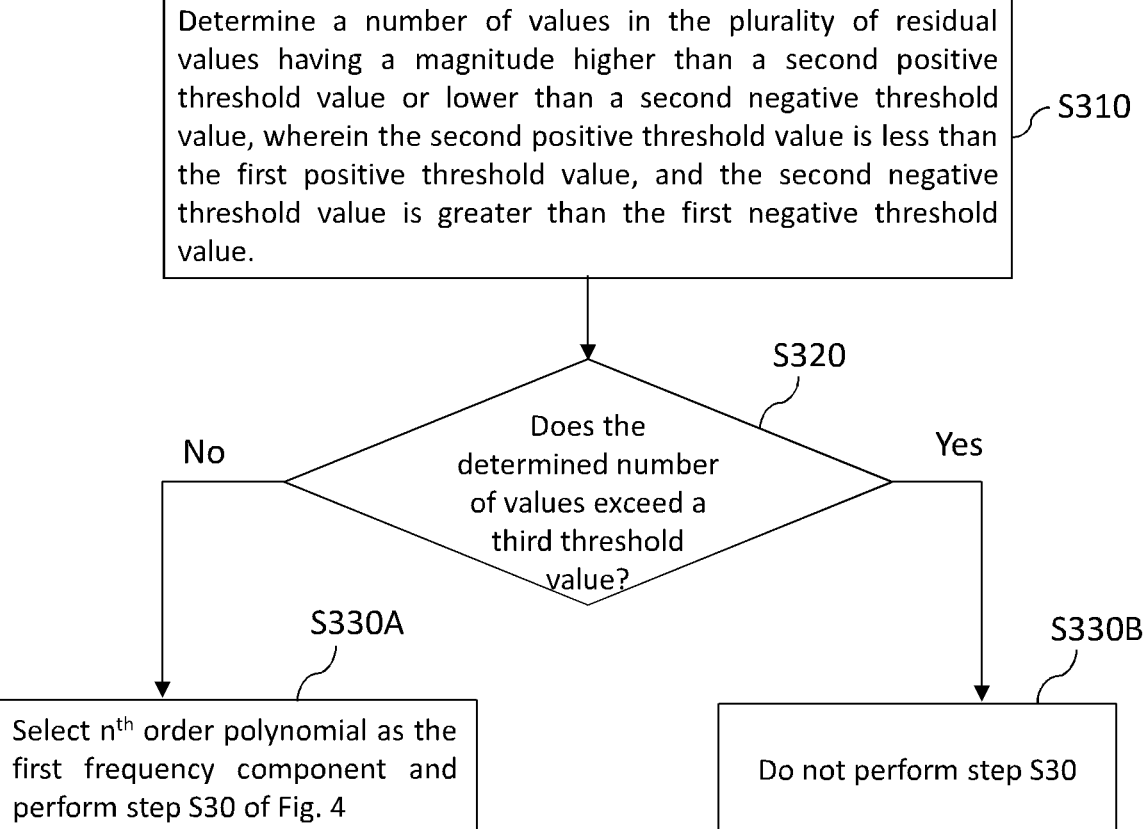

Determine a number of values in the plurality of residual values having a magnitude higher than a second positive threshold value or lower than a second negative threshold value, wherein the second positive threshold value is less than the first positive threshold value, and the second negative threshold value is greater than the first negative threshold value.

S310

S320

No

Yes

Does the determined number of values exceed a third threshold value?

S330A

S330B

Select $n^{th}$ order polynomial as the first frequency component and perform step S30 of Fig. 4

Do not perform step S30

Fig. 8

VOLUMETRIC OCT IMAGE DATA PROCESSING

This application claims the benefit of priority based on European Patent Application EP 20 207 153.6 filed Nov. 12, 2020, which is incorporated by reference herein in its entirety, as if set forth fully herein.

TECHNICAL FIELD

Example aspects herein generally relate to the field of ophthalmic optical coherence tomography (OCT) imaging systems and, more particularly, a method and apparatus for processing C-scan data generated by an OCT imaging system to generate correction data for compensating for axial displacements between B-scans in an acquired sequence of B-scans caused by a relative motion of the OCT imaging system and an imaging target that varies a distance therebetween during acquisition of the B-scans by the OCT imaging system.

BACKGROUND

The acquisition of a typical volumetric Optical Coherence Tomography (OCT) scan (also referred to as a C-scan) of a part of a subject's eye, such as the retina, can take approximately 1 to 5 seconds. During this time, an OCT beam is repeatedly scanned by the OCT imaging system in a first scan direction to record a sequence of (two-dimensional) B-scans, each of which comprises a series of axial scans (A-scans) that are recorded at respective points on the surface of the retina along the first scan direction. The B-scans in the sequence of B-scans are normally arrayed in a direction perpendicular to the first direction. During the acquisition of a C-scan, the eye might move axially (along the direction of the OCT beam), usually due to involuntary movements of the subject. For successful rendering of a C-scan image, and to ensure accuracy of subsequent measurements performed on the basis of the C-scan image, it may be necessary to correct for motion artefacts that are caused by the motion of the subject during the capture of the C-scan. If compensation is not performed on B-scan data to correct for an axial shift between some B-scans, which is caused by the motion of subject, then the accuracy of retinal layer identification and subsequent diagnostic measurements may be adversely affected.

SUMMARY

The present inventors have devised, in accordance with a first example aspect herein, a method of processing a C-scan data, which comprises a sequence of B-scans of an imaging target, which has been acquired by an OCT imaging system, to generate correction data for compensating for axial displacements between B-scans in the sequence of B-scans caused by a relative motion of the OCT imaging system and the imaging target that varies a distance therebetween during acquisition of the B-scans by the OCT imaging system. The method comprises generating the correction data by determining, for each pair of adjacent B-scans of a plurality of pairs of adjacent B-scans in the sequence, a respective indicator of an axial shift between respective representations of a common ocular feature in the adjacent B-scans. The method further comprises determining, from a variation of the determined indicators with locations of the corresponding pairs of adjacent B-scans in the sequence, a first frequency component of the variation which is indicative of the relative motion of the OCT imaging system and the imaging target during acquisition of the B-scans by the OCT imaging system.

The respective indicator of the axial shift may be determined for each pair of the adjacent B-scans by calculating a cross-correlation between the pair of adjacent B-scans and determining, as the indicator, an offset between the B-scans corresponding to a peak in the calculated cross-correlation.

Alternatively, the respective indicator of the axial shift may be determined for each pair of the adjacent B-scans by identifying respective locations of the common ocular feature in the B-scans of the pair of adjacent B-scans, and determining a displacement between the identified locations along an axis of the B-scans that is representative of an axial direction of the imaging system.

The method set out in the foregoing may further comprise determining a second frequency component of the variation which is indicative of a curvature of the imaging target. In this case, the second frequency component may be determined by fitting an $m^{th}$ order polynomial to the variation of the determined indicators, and the first frequency component may be determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

The method set out in the foregoing may further comprise using the correction data to compensate for the axial displacements between the B-scans in the sequence of B-scans caused by the relative motion of the OCT imaging system and the imaging target (20), by applying offsets based on the first frequency component to B-scans in the sequence of B-scans. In this case, the first frequency component may be determined by further performing at least two iterations of a process comprising steps of:

(i) calculating a plurality of residual values, each residual value calculated as a difference between an indicator in a variation of indicators and a corresponding value of an $n^{th}$ order polynomial;

(ii) determining whether the plurality of residual values comprise an outlier value which exceeds a first positive threshold value or falls below a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the $n^{th}$ order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process. The method may further comprise: determining a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than the third threshold value, compensating for the axial displacements between the B-scans in the sequence of B-scans, by applying offsets based on the first frequency component to B-scans in the sequence of B-scans; and in a case where the determined number of residual values is not smaller than the third threshold value, determining not to compensate for the axial displacements between the B-scans in the sequence of B-scans.

The method set out in the foregoing may further comprise generating a reliability indicator, which indicates a reliability of the generated correction data, by: calculating, using pairs of B-scans in the sequence of B-scans, respective values of a metric which are indicative of at least one of a speed and an acceleration of the imaging target structure relative to the OCT imaging system when the pairs of B-scans were acquired; determining if at least a predetermined number of the calculated values of the metric exceed a fourth threshold value; in a case where at least the predetermined number of calculated values of the metric are determined to exceed the fourth threshold value, setting the reliability indictor to indicate that the correction data is unreliable; and in a case where at least the predetermined number of calculated values of the metric are determined to not exceed the fourth threshold value, setting the reliability indictor to indicate that the correction data is reliable. The method may further comprise, in a case where the reliability indicator has been set to indicate that the correction data is reliable, compensating for the axial displacements between the B-scans in the sequence of B-scans by applying offsets based on the first frequency component to B-scans in the sequence of B-scans.

Furthermore, the present inventors have devised, in accordance with a second example aspect herein, a computer program comprising computer program instructions which, when executed by a processor, cause the processor to execute the method set out above.

Furthermore, the present inventors have devised, in accordance with a third example aspect herein, a data processing apparatus configured to process C-scan data, which comprises a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system. The data processing apparatus comprises an axial shift determination module arranged to determine, for each pair of adjacent B-scans of a plurality of pairs of adjacent B-scans in the sequence, a respective indicator of an axial shift between respective representations of a common ocular feature in the adjacent B-scans. The data processing apparatus further comprises a frequency component determination module, which is arranged to determine, from a variation of the determined indicators that is indicative of how the axial shifts vary with locations of the corresponding pairs of adjacent B-scans in the sequence, a first frequency component of the variation, which is indicative of the relative motion of the OCT imaging system and the imaging target during acquisition of the B-scans by the OCT imaging system.

The axial shift determination module may be arranged to determine the respective indicator of the axial shift for each pair of the adjacent B-scans by calculating a cross-correlation between the pair of adjacent B-scans and determining, as the indicator, an offset between the B-scans corresponding to a peak in the calculated cross-correlation. Alternatively, the axial shift determination module may be arranged to determine the respective indicator of the axial shift for each pair of the adjacent B-scans by identifying respective locations of the common ocular feature in the B-scans of the pair of adjacent B-scans, and determining a displacement between the identified locations along an axis of the B-scans that is representative of an axial direction of the imaging system.

The frequency component determination module may be further arranged to determine a second frequency component of the variation, which is indicative of a curvature of the imaging target. In this case, the frequency component determination module may be arranged to: determine the second frequency component by fitting an $m^{th}$ order polynomial to the variation of determined indicators; and determine the first frequency component by subtracting values of the $m^{th}$ order polynomial from the indicators in the variation of the determined indicators to generate a corrected variation of indicators, and fit an $n^{th}$ order polynomial to the corrected variation of indicators, wherein m and n are integers and m is smaller than n.

The data processing apparatus set out above may further comprise a displacement compensation module, which is arranged to compensate for the displacements between the B-scans in the sequence of B-scans caused by the relative motion of the OCT imaging system and the imaging target during acquisition of the B-scans by the OCT imaging system, by applying offsets based on the first frequency component to B-scans in the sequence of B-scans.

The frequency component determination module may be arranged to determine the first frequency component by further performing at least two iterations of a process comprising steps of:

(i) calculating a plurality of residual values, each residual value calculated as a difference between an indicator in a variation of indicators and a corresponding value of an $n^{th}$ order polynomial;

(ii) determining whether the plurality of residual values comprise an outlier value which exceeds a first positive threshold value or falls below a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the n-th order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process. The frequency component determination module is further configured to: determine a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than the third threshold value, compensate for the axial displacements between the B-scans in the sequence of B-scans, by applying offsets based on the first frequency component to B-scans in the sequence of B-scans; and in a case where the determined number of residual values is not smaller than the third threshold value, determine not to compensate for the axial displacements between the B-scans in the sequence of B-scans.

The data processing apparatus set out above may further comprise a reliability indicator generator module, which is configured to: calculate, using pairs of B-scans in the sequence of B-scans, respective values of a metric that are indicative of at least one of a speed and an acceleration of the imaging target structure relative to the OCT imaging system when the pairs of B-scans were acquired; determine if at least a predetermined number of the calculated values of the metric exceed a fourth threshold value; in a case where at least the predetermined number of calculated values of the metric are determined to exceed the fourth threshold value, set the reliability indictor to indicate that the correction data is unreliable; and in a case where at least the predetermined number of calculated values of the metric are determined to not exceed the fourth threshold value, set the reliability indictor to indicate that the correction data is reliable. In a case where the reliability indicator has been set to indicate that the correction data is reliable, the displacement compensation module may be configured to compensate for the axial displacements between the B-scans in the sequence of B-scans by applying offsets based on the first frequency component to B-scans in the sequence of B-scans.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 4 is a flow diagram illustrating a method by which the data processing apparatus of FIG. 1 processes C-scan data comprising a sequence of B-scans to generate correction data for compensating axial displacements between B-scans in the sequence of B-scans.

FIG. 6 illustrates a method which may be performed by a frequency determination module of the data processing apparatus to determine a first frequency component of the variation which is indicative of the relative motion of the OCT imaging system and the retina during the acquisition of the B-scans, in accordance with a first example implementation described herein.

FIG. 7 illustrates a method which may be performed by the frequency determination module to determine the first frequency component of the variation, which is indicative of the relative motion of the OCT imaging system and the retina during acquisition of the B-scans, in accordance with a second example implementation described herein.

FIG. 8 illustrates a method which can be performed to determine whether to compensate for the axial displacements between the B-scans in the sequence of B-scans, in accordance with an example embodiment herein.

DETAILED DESCRIPTION OF EXAMPLE EMBODIMENTS

Figure 1:
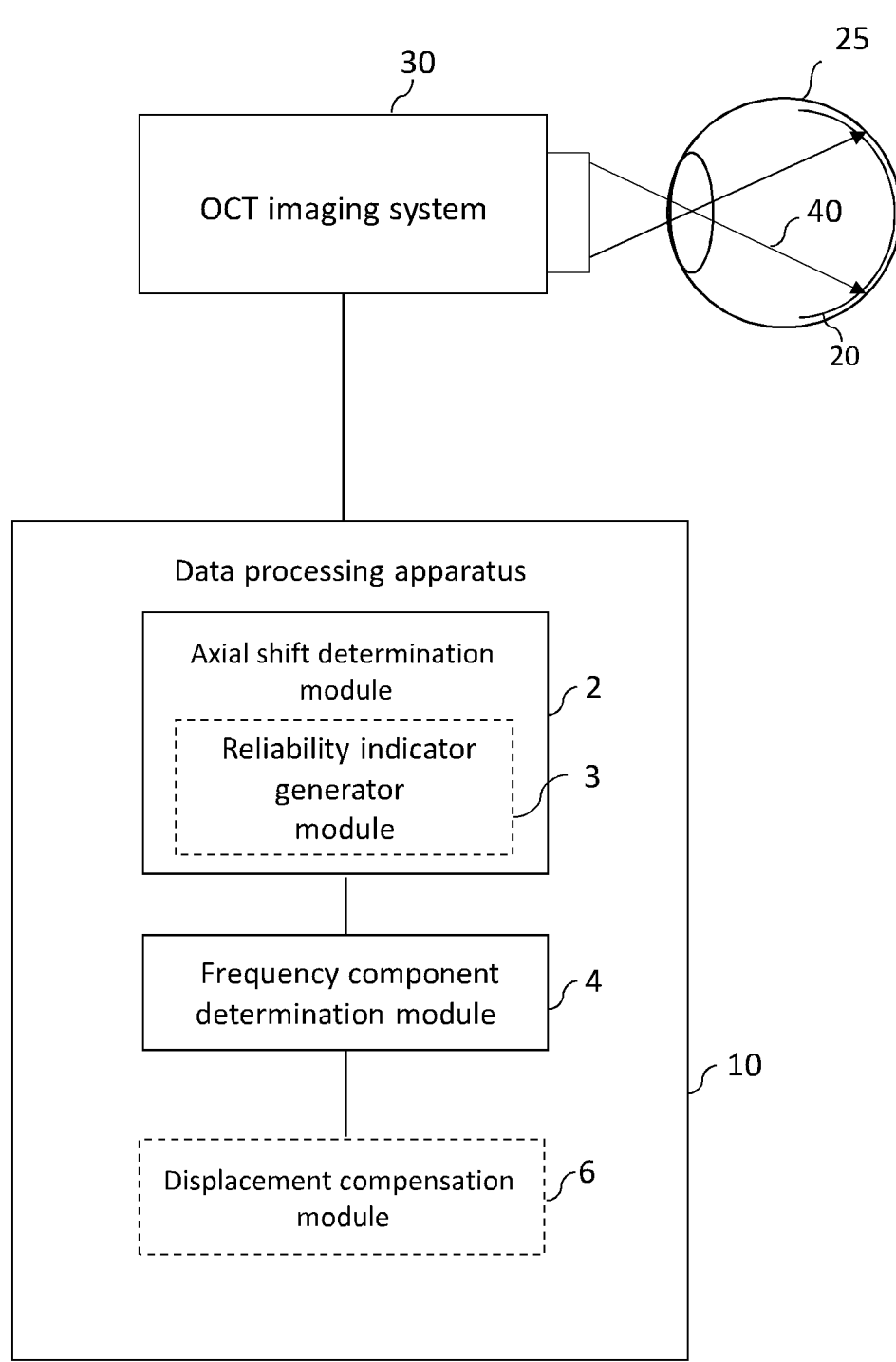
FIG. 1 is a schematic illustration of a data processing apparatus for processing C-scan data according to a first example embodiment herein.

FIG. 1 is a schematic illustration of a data processing apparatus 10 according to an example embodiment. The data processing apparatus 10 is configured to process C-scan data comprising a sequence of B-scans of an imaging target 20, which has been acquired by an OCT imaging system 30, to generate correction data for compensating for axial displacements between B-scans in the sequence of B-scans. The imaging target 20 may, as in the present example embodiment, be a retina of an eye 25 of a subject, but may alternatively be another part of the eye 25 which may have a curvature, such as an anterior region of the eye 25, for example. The axial displacements are caused by a relative motion of the OCT imaging system 30 and the imaging target 20, which varies a distance between the OCT imaging system 30 and the imaging target 20 during acquisition of the B-scans by the OCT imaging system 30. The axial displacement may be understood as a displacement along a propagation direction of an OCT light beam 40 that is incident on the eye 25 during use of the OCT imaging system 30 to image the retina.

The OCT imaging system 30 employs an ophthalmic scanner to scan the OCT imaging light beam 40 across the imaging target 20 to acquire the C-scan data, which is processed by the data processing apparatus 10. The data processing apparatus 10 may, as in the present example embodiment, be provided as a stand-alone processor such as a PC or laptop, which can be communicatively coupled to the OCT imaging system 30 (directly or via a network, such as the Internet) to receive C-scan data therefrom. Alternatively, the data processing apparatus 30 may be provided as part of the OCT imaging system 30. The OCT imaging system 30 may be any kind of OCT scanner well-known to those skilled in the art, which is capable of acquiring OCT data from the subject's eye 25.

As illustrated in FIG. 1, the data processing apparatus 10 of the present example embodiment comprises an axial shift determination module 2, which is configured to determine, for each pair of adjacent B-scans of a plurality of pairs of adjacent B-scans in the sequence of B-scans, a respective indicator of an axial shift between respective representations of a common ocular feature in the adjacent B-scans. The axial shift may, as in the present example embodiment, represent a shift (or offset) between the common ocular feature in the adjacent B-scans along an axis of the B-scans that corresponds to the axial direction (i.e. the direction in which the data in each A-scan of the A-scans, which make up the B-scan, is arrayed, the data having been obtained through measurements at various depths along the propagation direction of the OCT light beam 40 which is incident on the eye 25). In the present example embodiment, the sequence of B-scans that is processed by the axial shift determination module 2 comprises the complete sequence of B-scans forming the C-scan data that has been acquired by the OCT imaging system 30. However, it should be noted that the sequence of B-scans processed by the axial shift determination module 2 need not be the aforementioned complete sequence, and may alternatively comprise a subset of the complete sequence, for example a subset containing every other B-scan in the complete sequence of B-scans.

The axial shift determination module 2 may, as illustrated in FIG. 1, further comprise a reliability indicator generating module 3, whose functionality is described in more detail below.

The data processing apparatus 10 further comprises a frequency component determination module 4, which is configured to determine, from a variation of the determined indicators with locations of the corresponding pairs of adjacent B-scans in the sequence, a first frequency component of the variation which is indicative of the relative motion of the OCT imaging system 30 and the imaging target 20 during acquisition of the B-scans by the OCT imaging system 30.

The data processing apparatus 10 may, as in the present example embodiment, further comprise an axial displacement compensation module 6, which is arranged to use the correction data to compensate for the displacements between the B-scans in the sequence of B-scans caused by the relative motion of the OCT imaging system 30 and the imaging target 20 during acquisition of the B-scans by the OCT imaging system 30, specifically by applying offsets, which are based on the first frequency component, to B-scans in the sequence of B-scans.

A C-scan can be rendered to provide a three-dimensional image of a portion of the eye 25, and comprises a sequence of B-scans that are typically acquired by scanning the OCT light beam 40 in a raster pattern or the like across a two-dimensional region of the eye 25. Each B-scan is acquired by scanning the OCT light beam 40 in a single direction (for example, along an X-axis on the surface or the retina, for example) to record a two-dimensional, cross-sectional view (along the X and Z axes) of the region of the eye 25. Each B-scan comprises a plurality of A-scans, wherein each A-scan provides image data representing the axial/depth direction of the eye 25 (i.e. along the Z-axis) for a single lateral point in the eye 25.

Figure 2A:
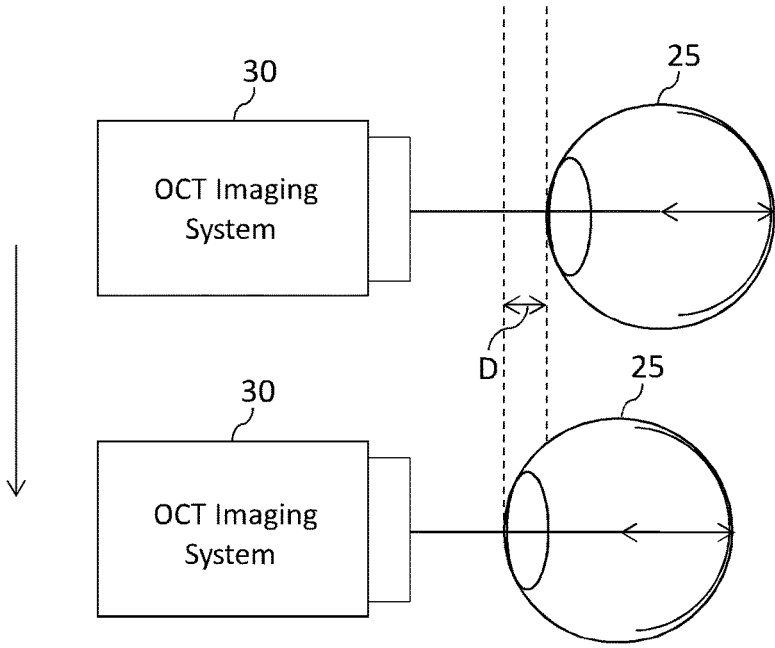
FIG. 2A illustrates an example of a movement of a subject which causes the distance between the subject's retina and an OCT imaging system to vary during imaging of the retina by the OCT imaging system.

FIG. 2A illustrates an example of a movement of the imaging target 20 (i.e. the retina, in the present example) relative to the OCT imaging system 30, which causes the distance between the retina and the OCT imaging system 30 to vary during the acquisition of C-scan data. As shown in the example of FIG. 2A, the motion of the subject during the acquisition of the B-scans causes the distance between the retina and the OCT imaging system 30 to be reduced by a distance D (along the axial direction).

Figure 2B:
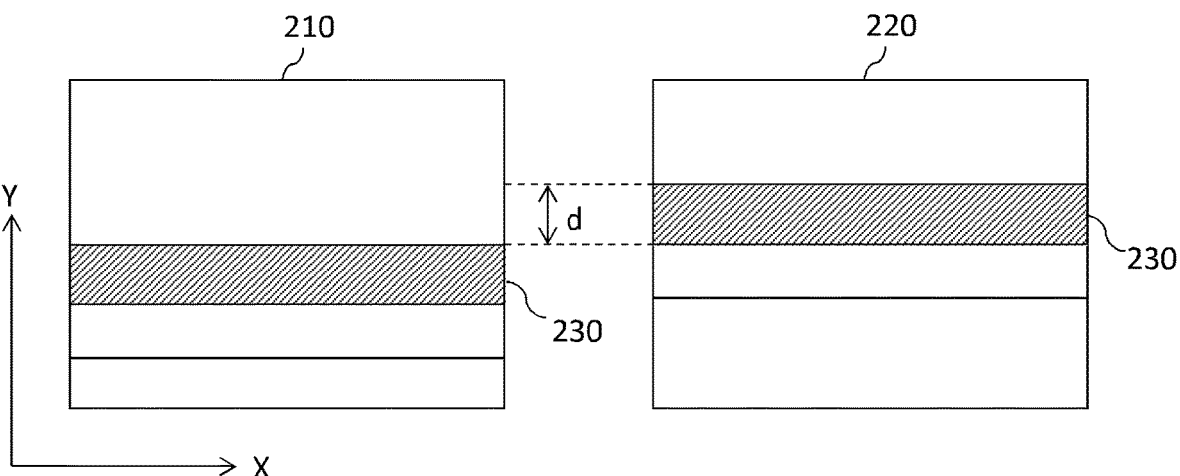
FIG. 2B illustrates an example of an axial shift between a common ocular feature in a pair of adjacent B-scans in a sequence of B-scans acquired by the OCT imaging system, the axial shift bein caused by the movement of the retina illustrated in FIG. 2A.

FIG. 2B illustrates an axial shift in the location of a common ocular feature, which is observed in a pair of adjacent B-scans, labelled 210 and 220, that have been captured before and after the relative movement of the eye 25 and the OCT imaging system 30 shown in FIG. 2A. In the present example, the common ocular feature in the pair of adjacent B-scans is a retinal layer 230 of the eye 25. As shown in FIG. 2B, due to the movement of the retina that occurs during the acquisition of the B-scans, the location of retinal layer 230 in B-scan 220 is offset by a distance of d pixels along the Y-axis of the B-scans relative to its location in B-scan 210. In FIG. 2B, the Y-axis of B-scans 210 and 220 represents the axial direction, while the X-axis represents a lateral direction along the surface of the retina. If uncorrected, the axial shift of the retinal layer 230 in the adjacent B-scans would cause motion artefacts to appear in renderings of the C-scan data, which may hinder a proper diagnosis or measurement of the underlying feature in the retina being performed.

Figure 3:
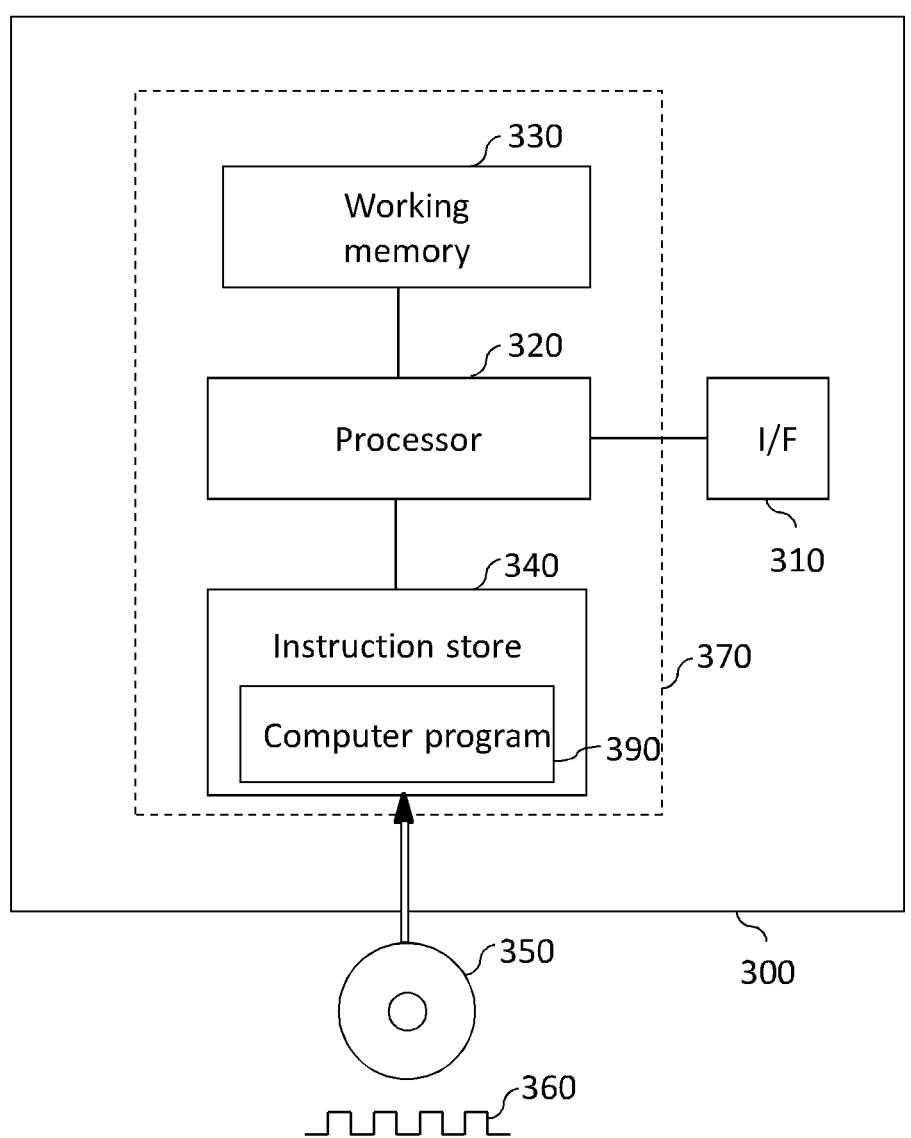
FIG. 3 is a block diagram illustrating an example implementation in programmable signal processing hardware of the data processing apparatus of the example embodiment herein.

FIG. 3 is a schematic illustration of a programmable signal processing hardware 300, which may be configured to process C-scan data using the techniques described herein and which can function as the axial shift determination module 2, the reliability indicator generator module 3, the frequency component determination module 4 and the displacement compensation module 6 of the first example embodiment.

The programmable signal processing apparatus 300 comprises a communication interface (I/F) 310, for communicating with the OCT imaging system 30 to receive C-scan data therefrom. The signal processing apparatus 300 further comprises a processor (e.g. a Central Processing Unit, CPU, and/or a Graphics Processing Unit, GPU) 320, a working memory 330 (e.g. a random access memory) and an instruction store 340 storing a computer program 390 comprising the computer-readable instructions which, when executed by the processor 320, cause the processor 320 to perform various functions including those of the axial shift determination module 2, the reliability indicator generator module 3, the frequency component determination module 4 and the displacement compensation module 6 described herein. The working memory 330 stores information used by the processor 320 during execution of the computer program 390. The instruction store 340 may comprise a ROM (e.g. in the form of an electrically-erasable programmable read-only memory (EEPROM) or flash memory) which is pre-loaded with the computer-readable instructions. Alternatively, the instruction store 340 may comprise a RAM or similar type of memory, and the computer-readable instructions of the computer program 390 can be input thereto from a computer program product, such as a non-transitory, computer-readable storage medium 350 in the form of a CD-ROM, DVD-ROM, etc. or a computer-readable signal 360 carrying the computer-readable instructions. In any case, the computer program 390, when executed by the processor 320, causes the processor 320 to execute a method of processing the C-scan data as described herein. It should be noted, however, that the axial shift determination module 2, the reliability indicator generator module 3, the frequency component determination module 4 and the displacement compensation module 6 may alternatively be implemented in non-programmable hardware, such as an application-specific integrated circuit (ASIC).

FIG. 4 is a flow diagram illustrating a method by which the data processing apparatus 10 of FIG. 1 processes C-scan data to generate correction data for compensating for axial displacements between B-scans in a sequence of acquired B-scans.

In step S10 of FIG. 4, the axial shift determination module 2 determines, for each pair of adjacent B-scans of a plurality of pairs of adjacent B-scans in the sequence, a respective indicator of an axial shift between respective representations of a common ocular feature in the adjacent B-scans. The respective indicator of the axial shift may, as in the present example embodiment, be a distance between the respective coordinates of the common ocular feature in the pair of adjacent B-scans, along an axis of the B-scans that corresponds to the axial direction described above. However, the indicator of the axial shift is not limited in this regard, and may alternatively be a value that is determined based on the distance. As an example, for a sequence of N+1 B-scans, $B_k$, for k=1, 2, . . . , N+1, it is possible to derive a set of N indicators $S_i$, for i=1, 2, . . . , N, from the N corresponding pairs of B-scans in the sequence of B-scans, wherein indicator $S_i$ is derived from B-scans $B_{k=i}$ and $B_{k=i+1}$, and is indicative of the axial shift between respective representations of a common ocular feature in the pair of B-scans $B_{k=i}$ and $B_{k=i+1}$. The indicator index i thus corresponds to the location of the pair of adjacent B-scans in the sequence of B-scans that yielded the indicator $S_i$.

The indicator of the axial shift may, as in the present example embodiment, be determined for each pair of adjacent B-scans by calculating a cross-correlation between the pair of adjacent B-scans and determining, as the indicator, an offset between the B-scans corresponding to a peak in the calculated cross-correlation. The cross-correlation may, for example, be a normalized two-dimensional cross-correlation of the pair of adjacent B-scans that determines an offset (along both axes of the B-scan) in the location of a representation of an ocular feature in one B-scan (of the pair of B-scans) relative to the location of a representation of the same ocular feature in the other B-scan. However, only the determined offset along an axis of the B-scan that corresponds to the axial direction may be taken as the indicator of the axial shift between respective representations of the common ocular feature in the pair of adjacent B-scans. In some circumstances, where lateral motion of the eye during the acquisition of the B-scans is negligible, a one-dimensional cross-correlation of the pair of adjacent B-scans may be performed, and the offset between the B-scans corresponding to a peak in the calculated one-dimensional cross-correlation may be taken as the indicator of the axial shift.

Although the indicator of the axial shift is calculated using cross-correlation in the present example embodiment, any other suitable method may alternately be employed. For example, in an alternative embodiment, the indicator of the axial shift may be determined for each pair of the adjacent B-scans by identifying respective locations of the common ocular feature in the B-scans of the pair of adjacent B-scans, and determining a displacement between the identified locations along an axis of the B-scans that corresponds to the axial direction as described above. The respective locations of the common ocular feature in the pair of adjacent B-scans may be identified, for example, using a machine-learning algorithm or any other suitable image processing algorithm.

In step S20 of FIG. 4, the frequency component determination module 4 determines, from a variation of the determined indicators with locations of the corresponding pairs of adjacent B-scans in the sequence of B-scans, a first frequency component of the variation, which is indicative of the relative motion of the OCT imaging system 30 and the imaging target 20 during acquisition of the B-scans by the OCT imaging system 30. The variation of the determined indicators with the locations of the corresponding pairs of adjacent B-scans in the sequence of B-scans may be understood as being representative of how the axial shift between each pair of adjacent B-scans in the sequence of B-scans varies with the location of the pair of B-scans in the sequence of B-scans. In other words, for the determined set of indicators $S_i$, i=1, 2, . . . , N, the variation of the determined indicators with locations of the corresponding pairs of adjacent B-scans in the sequence of B-scans, may be understood as the variation of the value of $S_i$ with the value of index i.

Figure 5:
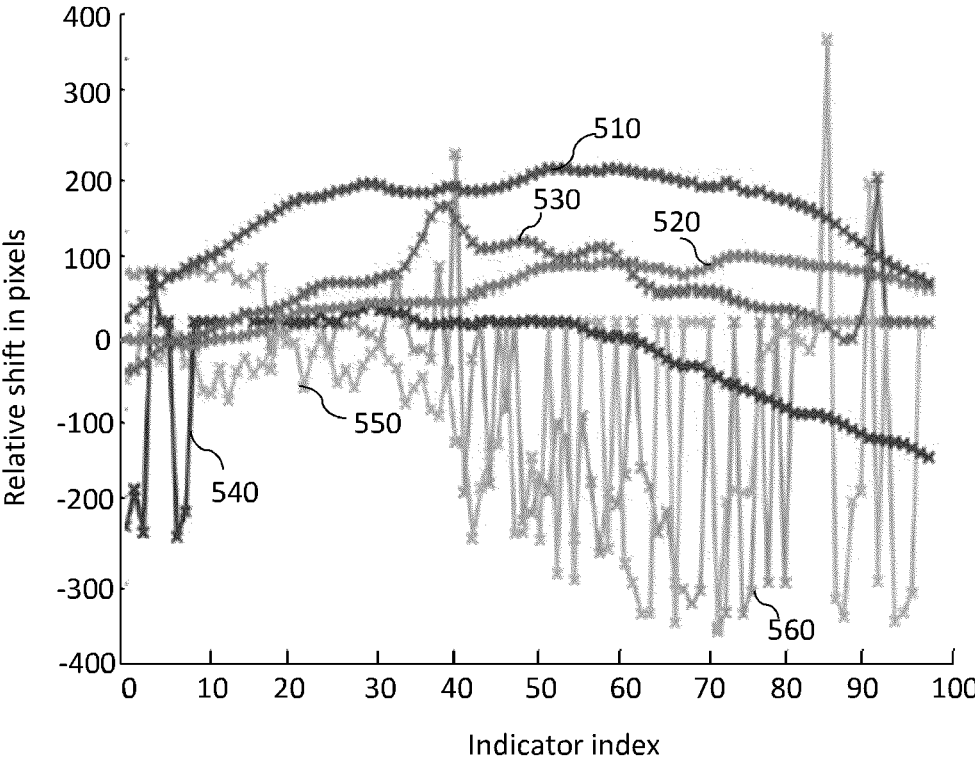
FIG. 5 illustrates plots of several sequences of indicator values, each indicator value indicating an axial shift between a common retinal feature in a pair of B-scans in the sequence of B-scans. The plots illustrate how the indicator values vary with the locations of the corresponding pairs of adjacent B-scans in the sequence.

FIG. 5 illustrates six example plots that correspond to six different sets of indicators determined from six different sequences of B-scans of the imaging target 20 in eye 25. Each plot illustrates the variation of determined indicators for a corresponding sequence of B-scans, wherein each indicator is calculated by cross-correlating a pair of adjacent B-scans in the sequence and is representative of an axial shift between the pair of adjacent B-scans. In the example of FIG. 5, the indicator determined for each pair of adjacent B-scans is plotted against indicator index i, that also corresponds to a pair of adjacent B-scans and is therefore representative the location of the pair of adjacent B-scans in the sequence of B-scans. As shown in FIG. 5, the variation of the determined indicators with the locations of the corresponding pairs of adjacent B-scans in the sequence of B-scans may comprise multiple frequency components attributed to different causes. For example, in addition to a frequency component that arises due to a relative motion of the eye 25 and the OCT imaging system 30 during the acquisition of the sequence of B-scans, the variation may also comprise various other frequency components such as, for example, a low-frequency component caused by a curvature of the retina, which can be observed in plots 510, 520 and 530. In particular, the frequency component resulting from the curvature of the retina may be lower than the frequency component caused by a motion of the eye 25, since the rate of axial shift of an ocular feature in a sequence of B-scans due to the curvature of the retina will likely be lower than the axial shift resulting from motion of the subject. Furthermore, the variation of indicators with the locations of the corresponding pairs of adjacent B-scans in the sequence, may also comprise high-frequency components resulting from spurious correlation between adjacent B-scans. Such high-frequency components can be observed in plots 540, 550 and 560, each of which displays a large number of peaks that contribute to the presence of high-frequency components in these variations of indictor values.

FIG. 6 illustrates a flow diagram of the steps which may be performed by the frequency determination module 4 to determine the first frequency component in step S20 of FIG. 4, in accordance with a first example implementation. In step S210 of FIG. 6, the frequency component determination module 4 determines a second frequency component of the variation, which is indicative of the curvature of the retina. The frequency component determination module 4 may, as in the present example, determine the second frequency component by fitting an $m^{th}$ order polynomial to the variation of the determined indicators, where m is an integer. For example, the sequence of determined indicators $S_i$, i=1, 2, . . . , N, may be represented as a set of N data points ($x_i$, $S_i$), i=1, 2, . . . , N. An $m^{th}$ order polynomial $P^m(x)$ may then be fitted to the sequence of indicators $S_i$, i=1, 2, . . . , N, by fitting the $m^{th}$ order polynomial to the set of equivalent datapoints $(x_i, S_i)$, i=1 to N, that represent the sequence of indicators, where $x_i$ is X-coordinate value associate with indicator $S_i$ in the data point $(x_i, S_i)$.

In step S220 of FIG. 6, the frequency determination module 4 subtracts values of the $m^{th}$ order polynomial from the indicators in the variation of the determined indicators to generate a corrected variation of the indicators. For example, for the sequence of determined indicators $S_i$, i=1, 2, . . . , N, represented in data point form $(x_i, S_i)$, i=1, 2, . . . , N, and for an $m^{th}$ order polynomial $P^m(x)$ fitted to the sequence of indicators, the corrected variation of the indicators may be given by the set of values, $C_i=S_i-P^m(x_i)$, i=1, 2, . . . , N. In the present example, the second frequency component of the variation that is indicative of the curvature of the retina is determined by fitting a $2^{nd}$ order polynomial to the variation of the determined indicators. However, depending on the expected curvature of the imaging target, a different order polynomial may be used. The $2^{nd}$ order polynomial may, as in the present example, be fitted using the least squares method to minimize a sum of squared residuals between the variation of the indicators and the $2^{nd}$ order polynomial, although any suitable polynomial regression method may otherwise be used. The $2^{nd}$ order polynomial that is representative of the curvature of the retina may be retained and later used for the rendering of the C-scan.

In step S230 of FIG. 6, the frequency determination module 4 determines the first frequency component of the variation of indicators by fitting an $n^{th}$ order polynomial to the corrected variation of the indicators $C_i$, i=1, 2, . . . , N, where n is an integer larger than m. The first frequency component, which is indicative of the relative motion of the OCT imaging system 30 and the imaging target 20, is thus represented by the $n^{th}$ order polynomial. As an example, the corrected variation of indicators $C_i$, i=1, 2, . . . , N, may be represented as data points $(x_i, C_i)$, i=1, 2, . . . , N and the $n^{th}$ order polynomial $P^n(x)$ may be fitted to the data points $(x_i, C_i)$, i=1, 2, . . . , N. In some embodiments, the frequency determination module 4 may first apply a smoothing operation (for example, by using a moving average filter) to the corrected variation of the indicators before fitting the $n^{th}$ order polynomial, in order to avoid overfitting to data points that result from spurious correlation. In the present example embodiment, a $5^{th}$ order polynomial is fitted to the corrected variation of the indicators as the $n^{th}$ order polynomial. However, the value of n is not limited in this regard, and may be selected in any suitable way. In some embodiments, the value of n may be selected based on scan parameters used by the OCT imaging system 30 to obtain the C-scan data, such as, the scan density (e.g. the number of B-scans captured per unit area of the retina) and the scan duration (i.e. the total time taken to acquire the C-scan data). As a general rule, a higher value of n may be selected for the $n^{th}$ order polynomial for a higher scan density and for longer scan durations.

Although the curvature of the retina is determined in the present example embodiment by fitting a low-order polynomial function to the variation of indicators, other methods may also be used instead. For example, the frequency component determination module 4 may alternatively determine the second frequency component, which is indicative of the curvature of the retina, by performing a discrete Fourier transform on the variation of indicators $(x_i, S_i)$, i=1, 2, . . . , N, to determine frequency domain samples for the variation of indicators. The frequency component determination module 4 may further extract a subset of the frequency domain samples that corresponds to a predetermined frequency range associated with the curvature of the retina. The frequency range may be determined empirically based on an expected curvature of the retina, for example. The frequency determination module 4 may further perform an inverse Fourier transform on the subset of frequency domain samples to obtain values corresponding to the second frequency component, which may be subtracted from the indicators in the variation of the determined indicators to generate the corrected variation of the indicators.

In some example embodiments, where the second frequency component only needs to be removed from the variation of indicators rather than extracted for later use, instead of performing an inverse Fourier transform on the subset of frequency domain samples and subtracting the obtained values corresponding to the second frequency component from the variation of indicators, the frequency component determination module 4 may instead process the frequency domain samples by setting to zero the subset of frequency domain samples and perform inverse Fourier transform on the processed frequency domain samples in order to directly obtain the corrected variation of the indicators. Alternatively, the frequency component determination module 4 may bandpass filter the variation of the indicators to remove the second frequency component corresponding to the curvature of the retina, in order to determine a corrected variation of indicators, and then fit the $n^{th}$ order polynomial to the corrected variation of the indicators. The lower cut-off frequency of the bandpass filtering process may be selected based on the expected curvature of the retina.

It should be noted, however, that in cases where the spatial extent of the scan is small relative to the curvature of the retina, the curvature of the retina can be assumed to be negligible and therefore, second frequency component need not be determined. In this case, the $n^{th}$ order polynomial may be fitted directly to the sequence of determined indicators $S_i$, i=1, 2, . . . , N, and determined as the first frequency component that is indicative of the relative motion of the OCT imaging system 30 and the imaging target 20.

Referring again to FIG. 4, in step S30, upon determining the first frequency component, the displacement compensation module 6 compensates for the displacements between the B-scans in the sequence of B-scans caused by the relative motion of the OCT imaging system 30 and the imaging target 20 during acquisition of the B-scans by the OCT imaging system 30 using the correction data, by applying offsets based on the first frequency component to B-scans in the sequence of B-scans. In the present example embodiment, the first frequency component is given by the $n^{th}$ order polynomial $P^n(x)$, and therefore, the displacement compensation module 6 may apply the offset by offsetting each B-scan in the sequence of B-scans based on a value of the $n^{th}$ order polynomial. For instance, for an $n^{th}$ order polynomial $P^n(x)$ that was fitted to the sequence of corrected variation of the indicators $C_i$, i=1, . . . , N (or, more specifically, fitted to the corresponding set of data points $(x_i, C_i)$, i=1, 2, . . . , N) in step S20 of FIG. 4, the set of values of $P^n(x_i)$, for i=1, 2, . . . , N, of the $n^{th}$ polynomial can be determined. A mapping between the set of values of $P^n(x_i)$, for i=1, 2, . . . , N and the B-scans in the sequence may be used, such that each value of the set of values $P^n(x_i)$, i=1, 2, . . . , N, is used to offset a B-scan in the sequence of B-scans. In the present example, as the indicator $S_i$ is derived from B-scans $B_{k=i}$ and $B_{k=i+1}$, then the polynomial value $P^n(x_i)$ may be used to offset the B-scan $B_{k=i+1}$. However, as each indicator is indicative of an axial shift between adjacent B-scans in the sequence, the offset applied to each B-scan $B_k$ in the sequence of B-scans must also include the cumulative sum of the offset applied to each preceding B-scan in the sequence (namely, B-scans in the sequence with an index lower than k). In other words, for each B-scan $B_k$ in the sequence, an offset of $$\sum\nolimits_{i=1}^{k-1} P''(x_i)$$

may applied to the B-scan in order to correct for axial displacement.

As an example, for a C-scan comprising of a sequence of 100 B-scans that are denoted by $B_k$, k=1 to 100, an $n^{th}$ order polynomial, $P''(x)$, may be determined from the variation of the indicators $S_i$, i=1, 2, . . . , 99 that is calculated from the 100 B-scans, by firstly subtracting the $m^{th}$ order polynomial, which is representative of the retinal curvature, from the variation of indicators, to obtain a corrected variation $C_i$, i=1, 2, . . . , 99 of indicators and then fitting the $n^{th}$ order polynomial to the corrected variation of indicators. The displacement compensation module 6 may further determine, from the corrected variation of indicators, the set of values $P''(x_i)$, i=1, 2, . . . , 99 of the $n^{th}$ order polynomial $P''(x)$. The set of values $P''(x_i)$, for I=1, 2, . . . , 99 may subsequently be used to offset B-scans, $B_k$, k=1 to 100, respectively. For example, the displacement compensation module 6 may compensate for the displacement between the 100 B-scans by offsetting B-scan $B_2$ by the value of $P''(x_1)$, offsetting B-scan $B_3$ by the value of $P''(x_1)+P''(x_2)$, and more generally, offsetting B-scan $B_k$ by an offset of $$\sum\nolimits_{i=1}^{k-1} P''(x_i).$$

It should be noted that, although the offsetting of the B-scans in step S30 of FIG. 4 is based on the values of the $n^{th}$ order polynomial, which was fitted to the sequence of corrected variation of the indicators $C_i$, i=1, . . . , N, in some other example embodiments, the sequence of corrected variation of the indicators $C_i$, i=1, N may be taken as the first frequency component and used to directly offset B-scans in the sequence of B-scans. For example, for each B-scan $B_k$ in the sequence, an offset of $$\sum\nolimits_{i=1}^{k-1} C_i$$

may applied to the B-scan in order to correct for axial displacements of the eye 25.

In some example embodiments, after fitting the $n^{th}$ order polynomial, the corrected variation of the indicators $C_i$, i=1, N is not used directly as the first frequency component to offset the B-scans in step S30 of FIG. 4. Instead, the frequency determination module 4 may determine the first frequency component in step S20 of FIG. 4 in accordance with a second example implementation, by further performing at least two iterations of a process comprising steps of:

(i) calculating a plurality of residual values, each residual value calculated as a difference between an indicator in a variation of indicators and a corresponding value of an $n^{th}$ order polynomial;

(ii) determining whether the plurality of residual values comprise an outlier value which exceeds a first positive threshold value or falls below a first negative threshold value;

(iii) in case the plurality of residual values is determined to comprise the outlier value, removing the indicator corresponding to the outlier value from the variation of indicators to generate an updated variation of indicators and, in case the plurality of residual values are determined not to comprise the outlier value, ending the process and determining the $n^{th}$ order polynomial as the first frequency component; and (iv) fitting the $n^{th}$ order polynomial to the updated variation of indicators.

Each residual value in the plurality of residual values is calculated in the first iteration of the above process as a difference between an indicator in the corrected variation of the indicators and a corresponding value of the $n^{th}$ order polynomial fitted to the corrected variation of the indicators. Furthermore, each residual value in the plurality of residual values is calculated in each iteration of remaining one or more iterations of the above process as a difference between an indicator in the updated variation of indicators generated in a previous iteration of the process and a corresponding value of the $n^{th}$ order polynomial fitted to the updated variation of indicators generated in the previous iteration of the process.

FIG. 7 is a flow diagram illustrating a process which may be performed by the frequency determination module 4 to determine the first frequency component in accordance with a second example implementation. As shown in FIG. 7, the frequency determination module 4 may first perform steps S210, S220 and S230 of the process described above with reference to FIG. 6. In the second example implementation, however, after the $n^{th}$ order polynomial is determined in step S230, the $n^{th}$ order polynomial is not used directly to offset the B-scans in step S30. Instead, the frequency determination module 4 further calculates, in step S240 of FIG. 7, a plurality of residual values, each residual value being calculated as a difference between an indicator in a variation of indicators and a corresponding value of an $n^{th}$ order polynomial. In the present example, where the corrected variation of indicators $C_i$, i=1, 2, . . . , N is represented as data points $(x_i, C_i)$, i=1, 2, . . . , N, and the $n^{th}$ order polynomial is denoted $P''(x)$, the plurality of residual values may be determined in step S240 of FIG. 7 as $R(x_i)=C_i-P''(x_i)$, for I=1, 2, . . . , N.

In step S250 of FIG. 7, the frequency determination module 4 determines whether the plurality of residual values comprise an outlier value which is higher than a first positive predetermined threshold value or lower than a first negative predetermined threshold value. In response to determining that the plurality of residual values comprise an outlier value, the frequency determination module 4 may, in step S260 of FIG. 7, remove the corrected indicator $C_i$ corresponding to the outlier value from the corrected variation of indicators $C_i$, i=1, 2, . . . , N to generate an updated variation of indicators $U_i$, for x=1 to N. Removing the corrected indicator $C_i$ corresponding to the outlier value may, for example, comprise setting the value of the corrected indicator $C_i$ to zero. For example, if it is determined that the residual value corresponding to corrected indicator $C_{i=p}$ is an outlier value, then the data point $(x_p, C_p)$ may be set to zero in the set of data points $(x_i, C_i)$, i=1, 2, . . . , N representing the corrected variation of indicators. It should be noted, however, that in some embodiments, instead of setting the corrected indicator $C_p$ corresponding to the outlier value to zero, the frequency determination module 4 may alternatively replace the corrected indicator $C_i$ corresponding to the outlier value with a new value, that may be based on one or more other values of $C_i$ that have residual values which are not determined as outliers at step S260, and obtained from these values by interpolation, for example.

In step S270 of FIG. 7, the frequency determination module 4 fits an $n^{th}$ order polynomial to the updated variation of indicators $U_i$, for x=1, 2, . . . , N. Then, the process of step S240 is repeated, this time to calculate a plurality of residual values, wherein each residual value is calculated as a difference between an indicator in the updated variation of indicators (determined in step S260) and a corresponding value of the $n^{th}$ order polynomial which has been fitted to the updated variation of indicators in step S270. After step S270 has been performed, steps S240, S250, S260 and S270 in FIG. 7 may be repeated until it is determined in step S250 that the plurality of residual values determined for an iteration does not contain an outlier value. In case that no outlier value is determined to be present in the plurality of residual values in step S250, then the process proceeds to step S250A, where the $n^{th}$ order polynomial that was used to generate the plurality of residual values is taken as the first frequency component, which is then used in step S30 of FIG. 4 to offset the B-scans in order to compensate for the displacements between the B-scans in the sequence of B-scans caused by the relative motion (in the axial direction) of the eye 25 and the OCT imaging system 30. In particular, the frequency determination module 4 may offset the B-scans based on the values of the $n^{th}$ order polynomial in the same manner as previously described for step S30 of FIG. 4.

In some example embodiments, when it is determined in step S250 of FIG. 7 that the plurality of residual values for an iteration does not contain any outlier, the frequency determination module 4 may further evaluate the plurality of residual values in order to determine whether the $n^{th}$ order polynomial that was used to obtain the plurality of residual values may be taken as the first frequency component and used to offset the B-scans in step S30 of FIG. 4. More specifically, referring to FIG. 8, the frequency determination module 4 may further determine, in step S310 of FIG. 8, a number of residual values among the plurality of residual values having a magnitude greater than a second positive threshold value or smaller than a second negative threshold value, wherein the second positive threshold value is smaller than the first positive threshold value in step S250 of FIG. 7; and the second negative threshold value is greater than the first negative threshold value in step S250 of FIG. 7. In step S320 of FIG. 8, the frequency determination module 4 determines if the number of residual values determined in step S310 of FIG. 8 exceeds a third threshold value. In response to determining that the number of residual values determined in step S310 of FIG. 8 does not exceed the third threshold value, the frequency determination module 4 selects, in step S330A of FIG. 8, and as the first frequency component, the $n^{th}$ order polynomial that was used to generate the plurality of residual values (which does not contain any outliers), and performs step S30 of FIG. 4 by using the $n^{th}$ order polynomial as the first frequency component. On the other hand, if the frequency determination module 4 determines that the number of residual values determined in step S310 of FIG. 8 does exceed the third threshold value, then step S30 of FIG. 4 is not performed. This is because, when a significant number of the residual values is relatively high, this can be taken to indicative a poor fit of the $n^{th}$ order polynomial to the corrected variation of indicators (or the updated variation of indicators). As such, instead of correcting the axial displacement in the sequence of B-scans using the $n^{th}$ order polynomial, the sequence of B-scans may be discarded, and new C-scan data comprising a new sequence of B-scans may be captured by performing a new OCT scan of the imaging target 20. The new sequence of B-scans may be processed using any of the foregoing methods to generate correction data for compensating for axial displacements between B-scans in the sequence of B-scans caused by a relative motion of the OCT imaging system 30 and the imaging target 20.

Referring again to FIG. 1, in example embodiments where the data processing apparatus 10 comprises a reliability indicator generator module 2 (for example, as part of the axial shift determination module 2, as in the present example embodiment, or as part of any other of the modules of the data processing apparatus 10, or as a stand-alone module), the reliability indicator generation module 3 may be configured to generate a reliability indicator which is indicative of whether or not the generated correction data is reliable. The reliability indicator may be used by the displacement compensation module 6 to determine whether to perform step S30 of FIG. 4, for example.

Figure 9:
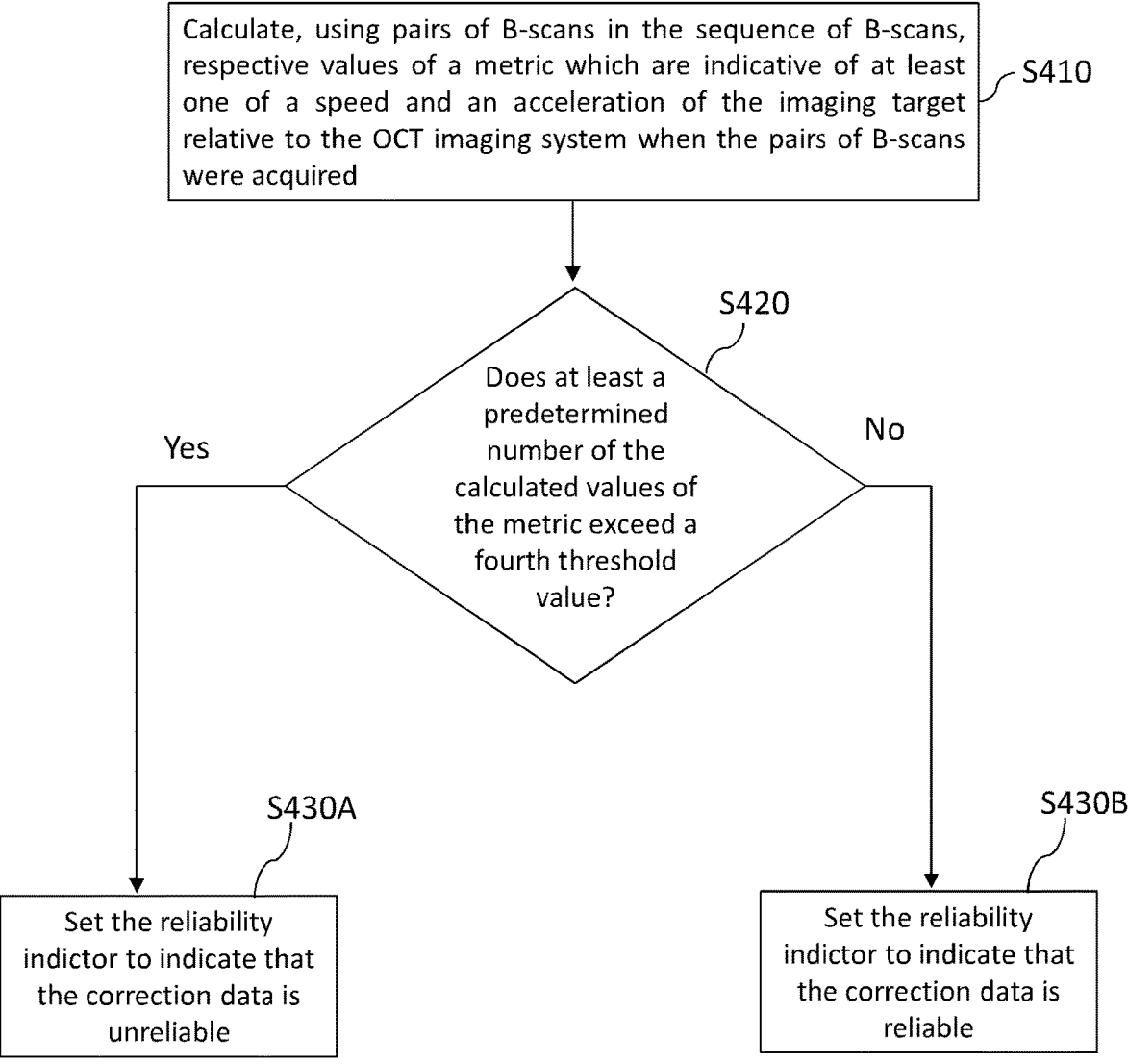
FIG. 9 illustrates a method which can be performed by a reliability indicator generating module, which may be provided as part of the data processing apparatus, to generate a reliability indicator which is indicative of a reliability of the generated correction data.

FIG. 9 is a flow diagram illustrating a process performed by the reliability indicator generation module 3 of FIG. 1 to generate the reliability indicator. In step S410 of FIG. 9, the reliability indicator generation module 3 calculates, using pairs of B-scans in the sequence of B-scans, respective values of a metric which are indicative of a speed and/or an acceleration of the imaging target 20 relative to the OCT imaging system 30 when the pairs of B-scans were acquired. The metric may, as in the present example embodiment, be a speed metric that is indicative of a speed (in the axial direction) of the imaging target 20 relative to the OCT imaging system 30. The speed metric may, as in the present example embodiment, be calculated using the indicators that have been determined in step S10 of FIG. 4 using adjacent pairs of B-scans in the sequence of B-scans. As each indicator is indicative of an axial shift of a common ocular feature in a pair adjacent B-scans, the indicator value, when divided by the time between the adjacent B-scans, is representative of the speed of the imaging target 20 relative to the OCT imaging system 30. However, it should be understood that the speed metric need not be calculated using on adjacent B-scans, and may instead be calculated based on an axial shift of a common ocular feature in a non-adjacent pair of B-scans in the sequence of B-scans. More generally, the determined axial shift of the common ocular feature in the pair of B-scans, divided by the time interval between the capture of the B-scans in the pair of B-scans, provides an indication of a rate of axial movement of the common ocular feature, and is therefore indicative of the speed of the relative motion of the imaging target 20 and the OCT imaging system 30. The metric may, as in the present example embodiment, be calculated for each adjacent pair of B-scans in the sequence, but may alternatively be calculated for only a subset of all acquired B-scan pairs, as previously mentioned.

In step S420 of FIG. 9, the reliability indicator generation module 3 determines if at least a predetermined number of calculated values of the metric exceed a threshold value. In the case that at least the predetermined number of calculated values of the metric is determined to exceed the threshold value, the reliability indicator generating module 3 sets (in step S430A of FIG. 9) the reliability indictor to indicate that the correction data is unreliable. On the other hand, in the case that fewer than the predetermined number of calculated values of the metric are determined in step S420 of FIG. 9 to exceed the threshold value, the reliability indicator generating module 3 sets the reliability indictor (in step S430B of FIG. 9) to indicate that the correction data is reliable. In the present example embodiment, where the metric is a speed metric, the threshold value used in step S420 of FIG. 9 may correspond to a maximum speed that is considered physically possible for the imaging target 20 during capture of the OCT C-scan data. Any calculated values of the metric that exceed this threshold may be considered anomalies that are caused by spurious correlation between B-scans, rather than actual relative motion of the imaging target 20 and the OCT imaging system 30. The predetermined number in step S420 of FIG. 9 may thus be set by the reliability indicator generating module 3 based on a maximum number of anomalies that can be accepted before the correction data is considered unreliable.

Although the metric is a speed metric in the present example embodiment, the metric calculated in step S410 of FIG. 9 may instead be an acceleration metric, which is indicative of the acceleration of the imaging target 20 relative to the OCT imaging system 30. When the metric is taken to be an acceleration metric in step S410, the threshold value set at step S420 may be set based on a maximum value of the acceleration that is considered realistic or physically possible. The reliability indicator generation module 3 may calculate the acceleration metric by determining a first value indicative of a rate of axial shift of a common ocular feature in a first pair of B-scans, and a second value indicative of a rate of axial shift of a common ocular feature in a second pair of B-scans, wherein the first pair differs from the second pair by at least one B-scan. The reliability indicator generation module 3 may further evaluate the acceleration metric based on a difference between the first value and the second value. For example, for a first pair of B-scans captured at times T1 and T2, and having a determined rate of axial shift value of A1, and a second pair of B-scans captured at times T3 and T4 (occurring after T1 and T2) and having a determined rate of axial shift of A2, the acceleration metric may be calculated as:

$$\frac{A2 - A1}{0.5(T4 + T3) - 0.5(T2 + T1)}$$

However, it should be understood that the acceleration metric is not limited to the above form and may be calculated based on a difference between A2 and A2, and another measure of the temporal separation of the two pairs of B-scans, for example T3–T1 or T4–T2.

Furthermore, in some example embodiments, the operation of the displacement compensation module 6 in step S30 of FIG. 4 to compensate for the axial displacements between the B-scans in the sequence of B-scans (caused by the relative motion of the OCT imaging system and the imaging target) may be conditional on the reliability indicator having been set to indicate that the correction data is reliable, such that step S30 of FIG. 4 is not performed where the reliability indictor is set to indicate that the correction data is unreliable at step S430A in FIG. 9.

Furthermore, in example embodiments like the present, in which the reliability indicator is generated and the process of FIG. 8 is performed, in the event that the reliability indicator has been set (in step S430A of FIG. 9) to indicate that the correction data is unreliable, a determination may be made by the displacement compensation module 6 not to perform step S30 even if has been determined at step S320 of FIG. 8 that the number of residual values in the plurality of residual values having a magnitude exceeding a second positive threshold value, or less than a second negative threshold value, is less than the third threshold value of step S320.

The example aspects described here avoid limitations, specifically rooted in computer technology, relating to conventional OCT data processing, which can yield rendered volumetric OCT data displaying motion artefacts that are typically caused by involuntary movements of a subject during the acquisition of volumetric OCT data. These motion artefacts can adversely affect the accuracy of ocular feature identification and any subsequent diagnostic measurements, for example. By virtue of the example aspects described herein, correction data for compensating for axial displacements between B-scans in a sequence of B-scans forming a C-scan, which can be caused by a relative motion of the OCT imaging system and the imaging target, is generated. In particular, for each pair of adjacent B-scans in a sequence of B-scans, a respective indicator of an axial shift between respective representations of a common ocular feature in the adjacent B-scans is determined. Furthermore, a frequency component indicative of the relative motion during the acquisition of the C-scan is extracted from a variation of the determined indicators with locations of the corresponding pairs of adjacent B-scans in the sequence. As a result, when the correction data is used to compensate for axial displacements between B-scans, a C-scan of the target imaging structure can be more accurately rendered. Furthermore, in at least some example embodiments, a frequency component corresponding to a curvature of the imaging target structure is extracted from the variation of determined indicators. This extracted curvature information can be retained and used for accurate rendering of the C-scan. In addition, in at least some example embodiments, the quality of the correction data can be estimated by determining a reliability indicator that is based on a metric indicative of at least a speed or an acceleration of the relative motion. Furthermore, in at least some example embodiments, the residue of a polynomial fit to the determined variation of indicators is used to estimate a quality of the correction data, and thus determine whether compensation should be performed using the correction data. Accordingly, the processing of B-scans to compensate for axial displacement between B-scans can be improved, as only reliable correction data may be used to compensate for the axial displacements. Also, by virtue of the foregoing capabilities of the example aspects described herein, which are rooted in computer technology, the example aspects described herein improve computers and computer processing/functionality, and also improve the field(s) of at least image processing, optical coherence tomography (OCT) and data processing, and the processing of OCT image data.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g. program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/ storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/ archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects herein, as described above.

Included in the programming and/or software of the system are software modules for implementing the procedures described herein. In some example embodiments herein, a module includes software, although in other example embodiments herein, a module includes hardware, or a combination of hardware and software.

While various example embodiments have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limiting, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A method of processing C-scan data, which comprises a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, the method comprising generating the correction data by:

determining, for each pair of adjacent B-scans of a plurality of pairs of adjacent B-scans in the sequence, a respective indicator of an axial shift between respective representations of a common ocular feature in the adjacent B-scans, wherein a variation of the determined indicators with locations of the corresponding pairs of adjacent B-scans in the sequence is defined by a set of frequency components of the variation; and determining, from the variation of the determined indicators with locations of the corresponding pairs of adjacent B-scans in the sequence, a first frequency component of the set of frequency components, the first frequency component being indicative of the relative motion of the OCT imaging system and the imaging target during acquisition of the B-scans by the OCT imaging system.

2. The method according to claim 1, wherein the respective indicator of the axial shift is determined for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans corresponds to an axial direction of the imaging system.

3. The method according to claim 1, wherein the method further comprises determining a second frequency component of the variation that is indicative of the curvature of the imaging target by fitting an $m^{th}$ order polynomial to the variation of the determined indicators, and the first frequency component is determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

4. The method according to claim 1, further comprising using the correction data to compensate for the axial displacements between the B-scans in the sequence of B-scans caused by the relative motion of the OCT imaging system and the imaging target, by applying offsets based on the first frequency component to B-scans in the sequence of B-scans.

5. The method according to claim 3, wherein the first frequency component is determined by further performing at least two iterations of a process comprising steps of:

(i) calculating a plurality of residual values, each residual value calculated as a difference between an indicator in a variation of indicators and a corresponding value of an $n^{th}$ order polynomial;

(ii) determining whether the plurality of residual values comprise an outlier value which exceeds a first positive threshold value or falls below a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the $n^{th}$ order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process.

6. The method of claim 5, further comprising:

determining a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value;

in a case where the determined number of residual values is smaller than the third threshold value, compensating for the axial displacements between the B-scans in the sequence of B-scans, by applying offsets based on the first frequency component to B-scans in the sequence of B-scans; and in a case where the determined number of residual values is not smaller than the third threshold value, determining not to compensate for the axial displacements between the B-scans in the sequence of B-scans.

7. The method according to claim 1, further comprising generating a reliability indicator, which indicates a reliability of the generated correction data, by:

calculating, using pairs of B-scans in the sequence of B-scans, respective values of a metric which are indicative of at least one of a speed and an acceleration of the imaging target structure relative to the OCT imaging system when the pairs of B-scans were acquired;

determining if at least a predetermined number of the calculated values of the metric exceed a fourth threshold value;

in a case where at least the predetermined number of calculated values of the metric are determined to exceed the fourth threshold value, setting the reliability indictor to indicate that the correction data is unreliable; and in a case where at least the predetermined number of calculated values of the metric are determined to not exceed the fourth threshold value, setting the reliability indictor to indicate that the correction data is reliable.

8. The method according to claim 7, further comprising, in a case where the reliability indicator has been set to indicate that the correction data is reliable, compensating for the axial displacements between the B-scans in the sequence of B-scans by applying offsets based on the first frequency component to B-scans in the sequence of B-scans.

9. A non-transitory, computer-readable storage medium storing computer program instructions which, when executed by a processor, cause the processor to execute a method of processing C-scan data, which comprises a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, the method comprising generating the correction data by:

determining, for each pair of adjacent B-scans of a plurality of pairs of adjacent B-scans in the sequence, a respective indicator of an axial shift between respective representations of a common ocular feature in the adjacent B-scans, wherein a variation of the determined indicators with locations of the corresponding pairs of adjacent B-scans in the sequence is defined by a set of frequency components of the variation; and determining, from the variation of the determined indicators with locations of the corresponding pairs of adjacent B-scans in the sequence, a first frequency component of the set of frequency components, the first frequency component being indicative of the relative motion of the OCT imaging system and the imaging target during acquisition of the B-scans by the OCT imaging system.

10. A data processing apparatus configured to process C-scan data, which comprises a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, the data processing apparatus comprising:

an axial shift determination module arranged to determine, for each pair of adjacent B-scans of a plurality of pairs of adjacent B-scans in the sequence, a respective indicator of an axial shift between respective representations of a common ocular feature in the adjacent B-scans, wherein a variation of the determined indicators with locations of the corresponding pairs of adjacent B-scans in the sequence is defined by a set of frequency components of the variation; and a frequency component determination module arranged to determine, from the variation of the determined indicators with locations of the corresponding pairs of adjacent B-scans in the sequence, a first frequency component of the set of frequency components, the first frequency component being indicative of the relative motion of the OCT imaging system and the imaging target during acquisition of the B-scans by the OCT imaging system.

11. The data processing apparatus according to claim 10, wherein the axial shift determination module is arranged to determine the respective indicator of the axial shift for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans that is representative of an axial direction of the imaging system.

12. The data processing apparatus according to claim 10, wherein the imaging target has a curvature, and the frequency component determination module is further arranged to determine a second frequency component of the variation, which is indicative of the curvature of the imaging target.

13. The data processing apparatus according to claim 12, wherein the frequency component determination module is arranged to:

determine the second frequency component by fitting an $m^{th}$ order polynomial to the variation of determined indicators; and determine the first frequency component by subtracting values of the $m^{th}$ order polynomial from the indicators in the variation of the determined indicators to generate a corrected variation of indicators, and fit an $n^{th}$ order polynomial to the corrected variation of indicators, wherein m and n are integers and m is smaller than n.

14. The data processing apparatus according to claim 10, further comprising a displacement compensation module arranged to compensate for the displacements between the B-scans in the sequence of B-scans caused by the relative motion of the OCT imaging system and the imaging target during acquisition of the B-scans by the OCT imaging system, by applying offsets based on the first frequency component to B-scans in the sequence of B-scans.

15. The non-transitory, computer-readable storage medium according to claim 9, wherein the respective indicator of the axial shift is determined for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans corresponds to an axial direction of the imaging system.

16. The non-transitory, computer-readable storage medium according to claim 9, wherein the imaging target has a curvature, and the method further comprises:

determining a second frequency component of the variation which is indicative of the curvature of the imaging target.

17. The non-transitory, computer-readable storage medium according to claim 16, wherein the second frequency component is determined by fitting an $m^{th}$ order polynomial to the variation of the determined indicators, and the first frequency component is determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

18. The non-transitory, computer-readable storage medium according to claim 9, wherein the method further comprises using the correction data to compensate for the axial displacements between the B-scans in the sequence of B-scans caused by the relative motion of the OCT imaging system and the imaging target, by applying offsets based on the first frequency component to B-scans in the sequence of B-scans.

19. A data processing apparatus configured to process C-scan data, which comprises a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, the data processing apparatus comprising:

a storage device storing a computer program comprising instructions; and a computer processor arranged to execute the instructions to:

determine, for each pair of adjacent B-scans of a plurality of pairs of adjacent B-scans in the sequence, a respective indicator of an axial shift between respective representations of a common ocular feature in the adjacent B-scans, wherein a variation of the determined indicators with locations of the corresponding pairs of adjacent B-scans in the sequence is defined by a set of frequency components of the variation, and determine, from the variation of the determined indicators with locations of the corresponding pairs of adjacent B-scans in the sequence, a first frequency component of the set of frequency components, the first frequency component being indicative of the relative motion of the OCT imaging system and the imaging target during acquisition of the B-scans by the OCT imaging system.

20. The data processing apparatus according to claim 19, wherein the computer processor determines the respective indicator of the axial shift for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans that is representative of an axial direction of the imaging system.

21. The data processing apparatus according to claim 19, wherein the imaging target has a curvature, and the computer processor also is arranged to execute the instructions to determine a second frequency component of the variation, which is indicative of the curvature of the imaging target.

22. The data processing apparatus according to claim 21, wherein the computer processor determines the second frequency component by fitting an $m^{th}$ order polynomial to the variation of determined indicators, and the computer processor determines the first frequency component by subtracting values of the $m^{th}$ order polynomial from the indicators in the variation of the determined indicators to generate a corrected variation of indicators, and fit an $n^{th}$ order polynomial to the corrected variation of indicators, wherein m and n are integers and m is smaller than n.

23. The data processing apparatus according to claim 19, wherein the computer processor also is arranged to execute the instructions to compensate for the displacements between the B-scans in the sequence of B-scans caused by the relative motion of the OCT imaging system and the imaging target during acquisition of the B-scans by the OCT imaging system, by applying offsets based on the first frequency component to B-scans in the sequence of B-scans.

24. The method according to claim 1, wherein the first frequency component forms a polynomial function usable to transform each B-scan of the sequence of B-scans to compensate for relative motion of the OCT imaging system.

\* \* \* \* \*